United States Patent
Harvey (10) Patent No.: US 11,428,761 B2
(45) Date of Patent: Aug. 30, 2022

(54) PATIENT PROXIMITY-MODULATED SPECIFIC ABSORPTION RATE

(71) Applicant: KONINKLIJKE PHILIPS N.V., Eindhoven (NL)

(72) Inventor: Paul Royston Harvey, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1005 days.

(21) Appl. No.: 15/315,416

(22) PCT Filed: May 27, 2015

(86) PCT No.: PCT/EP2015/061754
§ 371 (c)(1),
(2) Date: Dec. 1, 2016

(87) PCT Pub. No.: WO2015/185421
PCT Pub. Date: Dec. 10, 2015

(65) Prior Publication Data
US 2017/0097396 A1    Apr. 6, 2017

(30) Foreign Application Priority Data

Jun. 4, 2014 (EP) ..................................... 14171089

(51) Int. Cl.
*G01R 33/32* (2006.01)
*G01R 33/28* (2006.01)
(Continued)

(52) U.S. Cl.
CPC ............ *G01R 33/32* (2013.01); *A61B 5/0035* (2013.01); *A61B 5/0077* (2013.01); *A61B 5/055* (2013.01);
(Continued)

(58) Field of Classification Search
CPC .......... A61B 2562/0257; A61B 5/0035; A61B 5/0077; A61B 5/0555; G01R 33/288; G01R 33/32; G01R 33/583; G01V 3/12
See application file for complete search history.

(56) References Cited

U.S. PATENT DOCUMENTS 7,282,914 B2    10/2007  Morich et al.
7,902,822 B2 *   3/2011  Fontius ................ G01R 33/288
                                              324/307
(Continued)

FOREIGN PATENT DOCUMENTS

DE    102012206922 A1 * 10/2013    ........... A61B 5/0555
DE    102012206922 A1   10/2013
(Continued)

OTHER PUBLICATIONS

P. Bottomley et al. "Estimating Radiofrequency Power Deposition in Body NMR Imaging" Magnetic Resonance in Med. vol. 2, p. 336-349 (1985).

*Primary Examiner* — Pascal M Bui Pho
*Assistant Examiner* — Alexei Bykhovski (57) ABSTRACT

A method of operating a magnetic resonance imaging system (10) includes adjusting a radio frequency excitation field B1 to be applied to a subject of interest (20) to be imaged. At least one position parameter (d) that is indicative of a position of at least the portion of the subject of interest (20) relative to at least one radio frequency transmit antenna (36) of the magnetic resonance imaging system (10) is determined. At least one radio frequency power-related parameter of radio frequency power to be fed to the at least one radio frequency transmit antenna (36) is adjusted in dependence of the at least one of the determined at least one position parameter (d) and a determined geometric dimension (w) of the subject of interest (20).

10 Claims, 4 Drawing Sheets

(51) Int. Cl.
*A61B 5/00* (2006.01)
*A61B 5/055* (2006.01)
*G01V 3/12* (2006.01)
*G01R 33/58* (2006.01)

(52) U.S. Cl.
CPC ......... *G01R 33/288* (2013.01); *G01R 33/583* (2013.01); *G01V 3/12* (2013.01); *A61B 2562/0257* (2013.01)

(56) References Cited

U.S. PATENT DOCUMENTS

| | | | |
|---|---|---|---|
| 8,911,709 | B2 | 12/2014 | Driehuys |
| 10,156,621 | B2 | 12/2018 | Zhai et al. |
| 2003/0098688 | A1 | 5/2003 | Brinker |
| 2005/0122108 | A1 | 6/2005 | Yasuhara |
| 2005/0218896 | A1* | 10/2005 | Gortler ................ A61B 5/055 324/318 |
| 2006/0197528 | A1 | 9/2006 | Bielmeier |
| 2009/0192384 | A1 | 7/2009 | Fontius |
| 2013/0053683 | A1 | 2/2013 | Hwang |
| 2013/0137942 | A1* | 5/2013 | Karo ................... A61B 5/0537 600/301 |
| 2013/0342198 | A1* | 12/2013 | Vester ............... G01R 33/3692 324/307 |
| 2013/0342851 | A1* | 12/2013 | Dresel ................. A61B 5/0064 356/601 |

FOREIGN PATENT DOCUMENTS

| | | |
|---|---|---|
| WO | 2013153493 A1 | 10/2013 |
| WO | 2013181703 A1 | 12/2013 |

* cited by examiner

PATIENT PROXIMITY-MODULATED SPECIFIC ABSORPTION RATE

CROSS REFERENCE TO RELATED APPLICATIONS

This application is a U.S. national phase application of International Application No. PCT/EP2015/061754, filed on May 27, 2015, which claims the benefit of EP Application Serial No. 14171089.7 filed on Jun. 4, 2014 and is incorporated herein by reference.

FIELD OF THE INVENTION

The invention pertains to a method of operating a magnetic resonance imaging system with regard to adjusting a radio frequency excitation field applied to a subject of interest to be imaged, and a magnetic resonance imaging system being operated by employing such a method.

BACKGROUND OF THE INVENTION

In the field of magnetic resonance imaging, subjects of interest to be imaged are exposed to radio frequency fields applied for exciting nuclei of or within the subject of interest prior to acquiring magnetic resonance signals from the excited nuclei. Safety requirements with regard to an upper limit of a specific absorption rate have to be observed.

The US-patent application US2005/0122108 discloses a magnetic resonance imaging apparatus provided with a contour detection unit which detects the contour of an object. Further a coil movement unit is provided to move the radio frequency coil on the basis of the detected contour.

SUMMARY OF THE INVENTION

It is desirable to operate a magnetic resonance imaging system such that safety requirements with regard to an upper limit of a specific absorption rate for a subject of interest being imaged are observed at any time.

It is therefore an object of the invention to provide a method of operating a magnetic resonance imaging system with regard to adjusting a radio frequency excitation field to be applied to the subject of interest to be imaged, wherein the magnetic resonance imaging system is configured for acquiring magnetic resonance images of at least a portion of the subject of interest.

The method comprises steps of determining at least one position parameter that is indicative of a position of at least the portion of the subject of interest relative to at least one radio frequency transmit antenna of the magnetic resonance imaging system; and adjusting at least one radio frequency power-related parameter of radio frequency power to be fed to the at least one radio frequency transmit antenna in dependence of at least one out of the determined at least one position parameter and a determined geometric dimension of the subject of interest.

The phrase "position parameter", as used in this application, shall be understood particularly as a parameter that is directly or indirectly indicative of a position of at least the portion of the subject of interest relative to the at least one radio frequency transmit antenna. In the indirect case, the position parameter may be indicative of a position of at least the portion of the subject of interest relative to a reference position, whose relative position to the at least one radio frequency transmit antenna, in turn, is known.

In this way, exposure of the subject of interest to a specific absorption rate that may be potentially hazardous to the subject of interest's health can reliably be prevented, irrespective of size, posture or relative position of the subject of interest to radio frequency transmit antennae of the magnetic resonance system.

The step of adjusting the at least one radio frequency power-related parameter may be carried out manually by an operator, or, preferably, it may be carried out automatically and less prone to human error, for instance by a control unit of the magnetic resonance imaging system, wherein the control unit is configured for directly or indirectly controlling the at least one radio frequency power-related parameter.

In a preferred embodiment of the method, the step of determining the at least one position parameter is carried out by employing a proximity detection unit having at least one proximity detector. The term "proximity detector", as used in this application, shall be understood particularly as a detector that is able to detect a position of an object without physical contact between the detector and the object. Preferably, the at least one proximity detector is selected out of a group formed by ultrasonic proximity detectors, optical (e.g. infrared) proximity detectors, in particular in proximity-sensing (diffused) arrangement, and is in general based on an optical or acoustic working principle. In one embodiment, the at least one proximity detector may be designed as a camera. The term "proximity detection unit" shall explicitly exclude a unit having a working principle that is based on magnetic resonance imaging.

Preferably, the at least one proximity detector is arranged in an entrance region of an examination space of a magnetic resonance scanning unit. The phrase "entrance region", as used in this application, shall be understood particularly as a volume that the patient has to cross before entering the examination space.

In a further preferred embodiment, the proximity detection unit includes at least two proximity detectors that are arranged to aim towards opposite halves of the subject of interest. The method further comprises a step of determining at least one lateral dimension of the subject of interest. The step of adjusting the at least one radio frequency power-related parameter of the radio frequency power to be fed to the at least one radio frequency transmit antenna further is carried out in dependence of both the determined at least one position parameter and the at least one lateral dimension of the subject of interest.

By that, exposure of the subject of interest to a specific absorption rate that may be potentially hazardous to the subject of interest's health can readily and reliably be avoided, irrespective of size, posture or relative position of the subject of interest.

In yet another preferred embodiment of the method, the steps of determining at least one position parameter that is indicative of a position of at least the portion of the subject of interest relative to at least one radio frequency transmit antenna of the magnetic resonance imaging system, and determining, via the at least two proximity detectors, at least one lateral dimension of the subject of interest are carried out for a plurality of locations of at least the portion of the subject of interest.

The method further comprises a step of obtaining data for generating a geometric outline of the subject of interest relative to the at least one radio frequency transmit antenna of the magnetic resonance imaging system from the position parameters and the lateral dimensions determined at the plurality of locations.

The determining of the position parameters and the lateral dimensions of the subject of interest for the plurality of locations may be carried out consecutively during a movement of the subject of interest relative to the proximity detectors by either moving the subject of interest or by moving the proximity detectors. Preferably, in case of a human subject of interest, the plurality of locations is arranged along a body axis of the human subject of interest.

In this way, using a suitable arrangement, the position of at least the portion of the subject of interest relative to the at least one radio frequency transmit antenna can easily be monitored and checked. The monitoring and checking may be carried out by an operator, or, preferably, it may be carried out automatically and less prone to human error, for instance by a control unit of the magnetic resonance imaging system.

In yet another embodiment, the method further comprises a step of determining, by making use of determined position parameters and lateral dimensions of the subject of interest, an expected specific absorption rate of radio frequency power to be transmitted by the at least one radio frequency transmit antenna. The determining is based on pre-determined relationships for the specific absorption rate being absorbed by the subject of interest having specified lateral dimensions, while being exposed to the transmitted radio frequency power at specified relative position parameters. The step of adjusting the at least one radio frequency power-related parameter of radio frequency power to be fed to the at least one radio frequency transmit antenna is carried out in dependence of the determined expected specific absorption rate.

The phrase "specific absorption rate", as used in this application, shall be understood particularly to encompass a whole-body specific absorption rate as well as a local specific absorption rate related to the portion of the subject of interest that is being imaged.

In this way, a subject-specific and position-specific estimate for an expected specific absorption rate can be estimated, which allows to carry out the step of adjusting the at least one radio frequency power-related parameter such that the radiofrequency excitation field is as large as possible for optimum signal-to-noise ratio, but is reliably kept below a maximum tolerable specific absorption rate.

In one embodiment, the step of adjusting the at least one radio frequency power-related parameter of radio frequency power to be fed to the at least one radio frequency transmit antenna comprises adjusting at least one out of the duty cycle of a radio frequency pulse sequence and a radio frequency power amplitude. By that, flexibility for adjusting radio frequency pulse sequences that are customary in the art of magnetic resonance imaging can be accomplished.

In another aspect of the invention, a magnetic resonance imaging system is provided that is configured for acquiring magnetic resonance images of at least a portion of a subject of interest. The magnetic resonance imaging system comprises a scanning unit that provides an examination space to position at least the portion of the subject of interest within, wherein the examination space has an entrance region for the subject of interest to enter the examination space, and the scanning unit further has a main magnet configured for generating a static magnetic field $B_0$ in the examination space;

a magnetic gradient coil system that is configured for generating gradient magnetic fields superimposed to the static magnetic field $B_0$;

at least one radio frequency transmit antenna that is configured for applying a radio frequency excitation field $B_1$ to nuclei of or within the portion of the subject of interest for magnetic resonance excitation;

at least one radio frequency receive antenna that is configured for receiving magnetic resonance signals from the nuclei of or within the portion of the subject of interest that have been excited by applying the radio frequency excitation field $B_1$;

a control unit configured for controlling functions of the magnetic resonance imaging system; and a proximity detection unit, including at least one proximity detector, that is configured for determining at least one position parameter which is indicative of a position of at least the portion of the subject of interest relative to the at least one radio frequency transmit antenna.

The control unit is configured to carry out steps of any of the methods disclosed before herein, or a combination thereof.

In this way, an exposure of the subject of interest to a radio frequency excitation field level beyond a maximum tolerable specific absorption rate can reliably be prevented during acquiring magnetic resonance images of at least the portion of the subject of interest.

In another preferred embodiment of the magnetic resonance imaging system, the proximity detection unit comprises at least one pair of proximity detectors that, in at least one state of operation, is arranged to aim towards the subject of interest from two intersecting directions that form angles of at least 45°.

By that, an improved subject-specific and position-specific estimate for an expected specific absorption rate can be estimated on the basis of a development of a cross-section of the subject of interest over the plurality of locations, which can be determined from lateral dimensions and position parameters of the subject of interest. The estimate of the expected specific absorption rate allows to carry out the step of adjusting the at least one radio frequency power-related parameter such that the radio frequency excitation field is as large as possible for optimum signal-to-noise ratio, but is reliably kept below a maximum tolerable specific absorption rate.

Furthermore, the determined cross-section of the subject of interest can enable the detection of limbs of the subject of interest touching the body, and/or of legs touching.

In yet another preferred embodiment of the magnetic resonance imaging system, the at least one proximity detector or the pair of proximity detectors is arranged in the entrance region of the scanning unit. In this way, the development of the cross-section over the plurality of locations can readily be determined during a positioning of the subject of interest within the examination space.

In another preferred embodiment of the magnetic resonance imaging system, the at least one proximity detector is designed as a camera. The camera may provide digital signals at an output port. Preferably, the camera is arranged outside the scanning unit, aiming towards the entrance region of the examination space. From pictures taken by the camera, position parameters of at least the portion of the subject of interest relative to the at least one radio frequency transmit antenna and lateral dimensions of the subject of interest can readily be obtained.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
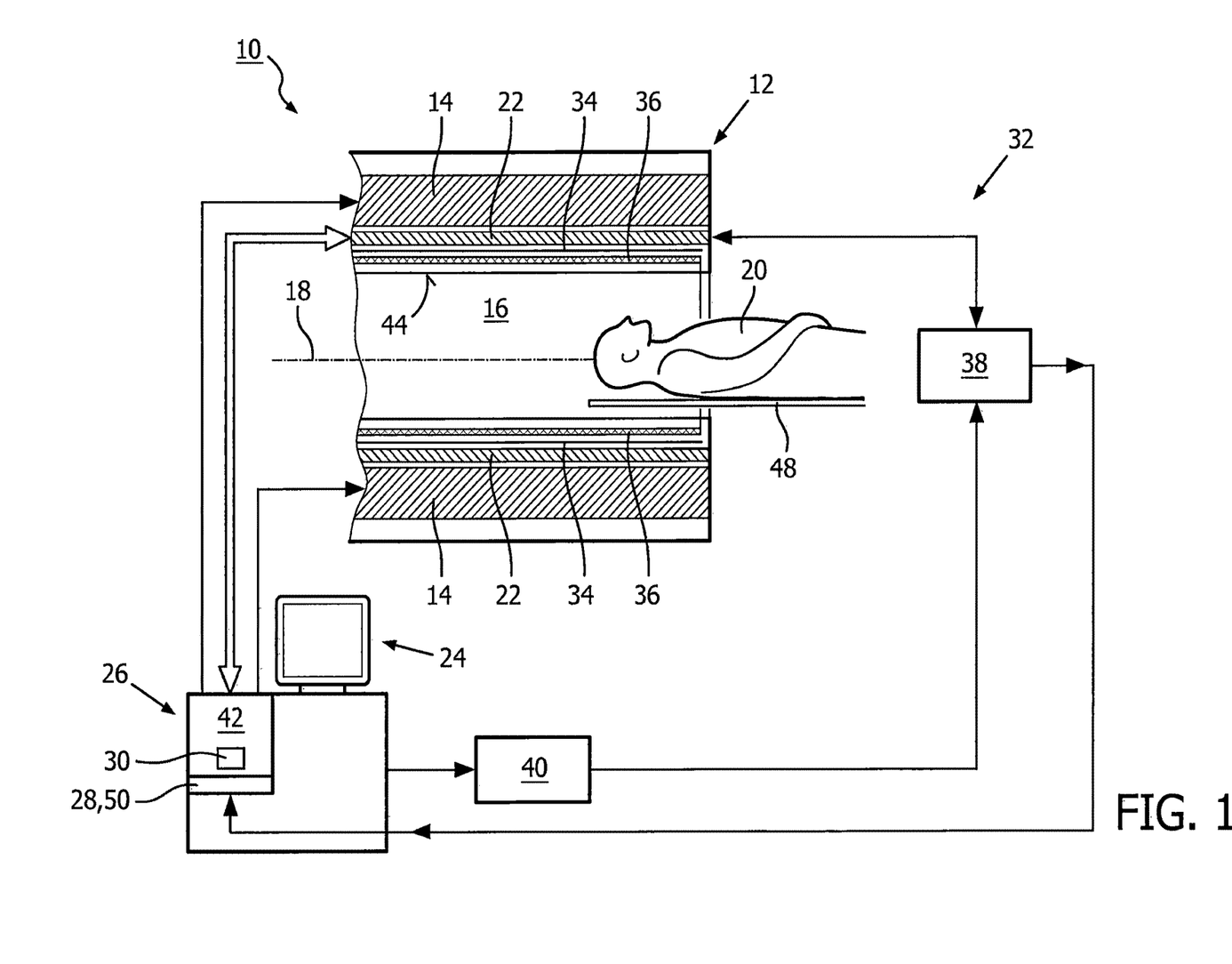
FIG. 1 shows a schematic illustration of a part of an embodiment of a magnetic resonance imaging system in accordance with the invention.

FIG. 1 shows a schematic illustration of a part of an embodiment of a magnetic resonance imaging system 10 configured for acquiring magnetic resonance images of at least a portion of a subject of interest 20, usually a patient. The magnetic resonance imaging system 10 comprises a scanning unit 12 having a main magnet 14. The main magnet 14 has a central bore that provides an examination space 16 around a center axis 18 for the subject of interest 20 to be positioned within. The examination space 16 is laterally limited by a wall 44 of the central bore. The examination space 16 has an entrance region 32 that the subject of interest 20 has to cross to enter the examination space 16. The main magnet 14 is provided for generating a static magnetic field $B_0$ at least in the examination space 16. The static magnetic field $B_0$ defines an axial direction of the examination space 16, aligned in parallel to the center axis 18. It is appreciated that the invention is also applicable to any other type of magnetic resonance imaging systems providing an examination region within a static magnetic field.

Further, the magnetic resonance imaging system 10 comprises a magnetic gradient coil system 22 configured for generating gradient magnetic fields superimposed to the static magnetic field $B_0$. The magnetic gradient coil system 22 is concentrically arranged within the bore of the main magnet 14, outside the examination space 16.

The magnetic resonance imaging system 10 comprises a control unit 26 configured to control functions of the magnetic resonance imaging system 10. The control unit 26 includes a human interface device 24 including a monitor unit having a touch-sensitive screen.

Furthermore, the magnetic resonance imaging system 10 includes a radio frequency antenna device 36 designed as a whole-body coil that is provided for applying a radio frequency excitation field $B_1$ to nuclei of or within the subject of interest 20 for magnetic resonance excitation during radio frequency transmit time periods to excite the nuclei of or within the subject of interest 20 for the purpose of magnetic resonance imaging. To this end, radio frequency power is fed, controlled by the control unit 26, from a radio frequency transmitter 40 to the whole-body coil. The radio frequency power is formed as a series of radio frequency pulse sequences having a duty cycle and a radio frequency power amplitude. As the person skilled in the art is familiar with a plurality of application-specific radio frequency pulse sequences, there is no need to describe specific properties of the radio frequency pulse sequences in detail.

The whole-body coil has a center axis and, in the operational state, is arranged concentrically within the bore of the main magnet 14, outside the examination space 16, such that the center axis of the whole-body coil and the center axis 18 of the scanning unit 12 coincide. As is well known in the art, a cylindrical metal radio frequency shield 34 is arranged concentrically between the magnetic gradient coil system 22 and the whole-body coil.

The whole-body coil is also provided for receiving magnetic resonance signals during radio frequency receive phases from the nuclei of or within the portion of the subject of interest 20 that have been excited by applying the radio frequency excitation field $B_1$. In an operational state of the magnetic resonance imaging system 10, radio frequency transmit phases and radio frequency receive phases are taking place in a consecutive manner.

The radio frequency transmitter 40 is configured, initiated and controlled by the control unit 26, to feed radio frequency power of a magnetic resonance radio frequency and in the form of radio frequency pulse sequences to the whole-body coil and the magnetic gradient coil system 22 via a radio frequency switching unit 38 during the radio frequency transmit phases. Each pulse sequence is configured to generate the radio frequency excitation field $B_1$ via the radio frequency transmit antenna 36 and magnetic gradient fields via the magnetic gradient coil system 22.

During the radio frequency receive phases, the radio frequency switching unit 40, controlled by the control unit 26, directs the magnetic resonance signals from the whole-body coil to a signal processing unit 42 residing in the control unit 26. The signal processing unit 44 is configured for processing acquired magnetic resonance signals to obtain magnetic resonance image data representative of magnetic resonance images of at least the portion of the subject of interest 20.

For a uniform radio frequency excitation field $B_1$ inside the subject of interest 20 it is found that the local specific absorption rate at a periphery of the subject of interest 20 is an approximate function of a lateral dimension w of the subject of interest 20. Thus, for subjects of interest 20 with a larger lateral dimension w, equal amplitudes $B_1^{rms}$ (rms: root mean square) of the radio frequency excitation field $B_1$ results in higher local specific absorption rates at the periphery, compared to a subject of interest 20' with a smaller lateral dimension w'. This is a consequence of a number of physical properties of the way the radio frequency excitation field $B_1$ is generated in a cylindrical radio frequency whole-body coil, such as a birdcage coil, commonly used as a radio frequency transmit antenna in a whole-body magnetic resonance imaging system. One specific property is that the electric field increases approximately linearly from the center axis 18 towards the radio frequency transmit antenna 36. Thus, for an equivalent amplitude $B_1^{rms}$, a larger diameter whole-body coil will generate a higher peak electric field at a center bore wall of the main magnet 14 compared to a smaller diameter central bore. In addition, a subject of interest 20' with a smaller lateral dimension w' that is positioned laterally off-center will also experience a higher peripheral local specific absorption rate due to the closer proximity to the radio frequency transmit antenna 36. As discussed before, subjects of interest 20 with large lateral dimensions w are consequently exposed to this higher electric field at their periphery and as the periphery approaches the center bore wall. In the ultimate limit, an amplitude $B_1^{rms}$ that realizes a safe peripheral local specific absorption rate for the one subject of interest 20' having lateral dimension w' may not be usable for a subject of interest 20 with another lateral dimension w because the generated peripheral local specific absorption rate will be above a maximum tolerable specific absorption rate. Also, a maximum tolerable specific absorption rate that is assumed to be safe for a subject of interest 20 positioned centrally in the bore of the main magnet 14 may not be safe when that same subject of interest 20 is placed laterally off-center.

In order to ensure a specific absorption rate applied to the subject of interest 20 during imaging that always falls below the maximum tolerable specific absorption rate, the magnetic resonance imaging system 10 is operated with regard to adjusting a radio frequency excitation field $B_1$ applied to the subject of interest 20 to be imaged pursuant to a method in accordance with the invention, which will be described later on.

The method comprises a step of determining lateral dimensions w of the subject of interest 20 and determining position parameters $d_i$ (FIG. 2) that are indicative of a position of at least the portion of the subject of interest 20 relative to the radio frequency transmit antenna 36 of the magnetic resonance imaging system 10.

The method further includes a step of adjusting at least one radio frequency power-related parameter of radio frequency power to be fed to the at least one radio frequency transmit antenna 36 in dependence of at least one out of the determined position parameters $d_i$ and the determined lateral dimensions $w_i$ of the subject of interest.

To this end, the magnetic resonance imaging system 10 is equipped with a proximity detection unit 46 comprising two proximity detectors $D_1$, $D_9$ designed as ultrasonic proximity sensors. The proximity detection unit 46 is configured for determining position parameters $d_i$ which are indicative of a position of at least the portion of the subject of interest 20 relative to the radio frequency transmit antenna 36, and for determining lateral dimensions $w_i$ of the subject of interest 20, as will be described later on.

Figure 2:
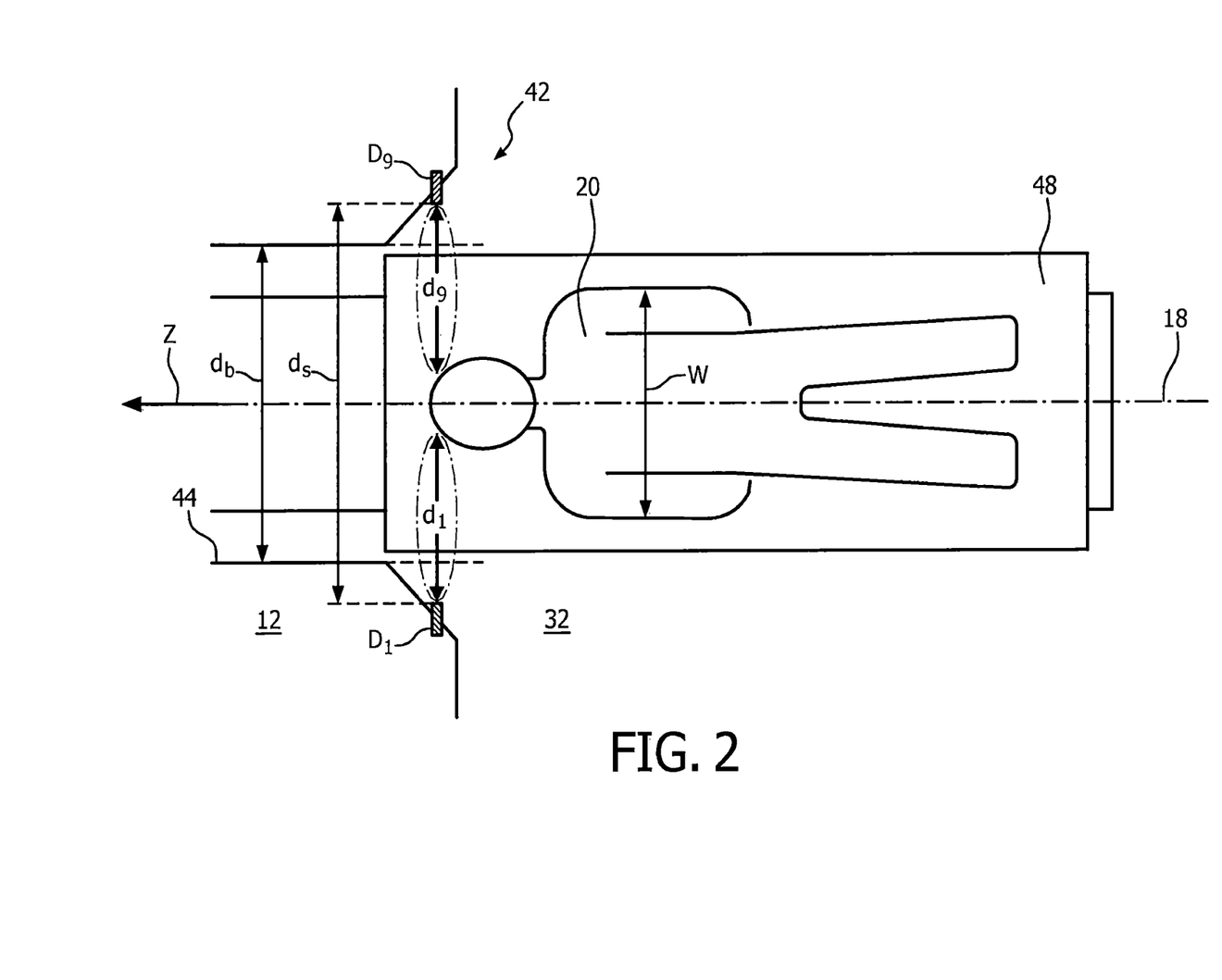
FIG. 2 is a top view of an entrance region of a scanning unit of the magnetic resonance imaging system pursuant to FIG. 1.

As shown in FIG. 2, the two proximity detectors $D_1$, $D_9$ are arranged in the entrance region 32 of the scanning unit 12. Each one of the two proximity detectors $D_1$, $D_9$ is aiming in a direction perpendicular to and towards the center axis 18. The aiming direction of the two proximity detectors $D_1$, $D_9$ is selected to be just above a space reserved for a patient table 48, which is provided to support the subject of interest 20 during imaging, to cross the entrance region 32. In this arrangement, the two proximity detectors $D_1$, $D_9$ will determine the proximity of the subject of interest 20 during the crossing of the entrance region 32 by the subject of interest 20 for positioning within the examination space 16. In this way, the two proximity detectors $D_1$, $D_9$ are arranged to aim towards opposite halves of the subject of interest 20. For instance, if the subject of interest 20 is in the supine position, the two proximity detectors $D_1$, $D_9$ would be aiming at the right side and the left side of the subject of interest 20, respectively, during the crossing of the entrance region 32 by the subject of interest 20. If the subject of interest 20 was lying on the side, the two proximity detectors $D_1$, $D_9$ would be aiming at the front side and the back side of the subject of interest 20, respectively.

Each one of the two proximity detectors $D_1$, $D_9$ provides an output signal via a suitable interface to an input port of the control unit 26 (not shown). The control unit 26 is configured for processing and for evaluating the output signals. Means for processing the output signals, for instance by filtering, amplifying and digitizing, are commonly known to the person skilled in the art and shall therefore not described in detail herein.

Referring now to FIG. 2, a distance $d_{left}$ of the left side of the subject of interest 20 to the main magnet center bore wall 44, as a function of the displacement z into the bore of the main magnet 14, is given by $$d_{left}(z) = d_9(z) - \frac{1}{2}(d_s - d_b)$$

wherein $d_s$ denotes the distance between the two proximity detectors $D_1$, $D_9$, $d_b$ the diameter of the bore of the main magnet 14 and $d_9$ the measured distance from the proximity detector $D_9$ arranged to the left of the subject of interest 20 to the subject of interest 20.

Likewise, for the right side of the subject of interest 20, a distance $d_{right}$ of the right side of the subject of interest 20 to the main magnet center bore wall 44, as a function of the displacement z into the bore of the main magnet 14, is given by $$d_{right}(z) = d_1(z) - \frac{1}{2}(d_s - d_b)$$

wherein $d_1$ denotes the measured distance from the proximity detector $D_1$ arranged to the right of the subject of interest 20 to the subject of interest 20.

A lateral dimension of the subject of interest 20 given by a width w can be obtained from distances $d_1$, $d_9$ corresponding to the signals of the proximity detectors $D_1$, $D_9$ by $$w(z)=d_b-d_{left}(z)-d_{right}(z)=d_s-d_1(z)-d_9(z)$$

Figure 3:
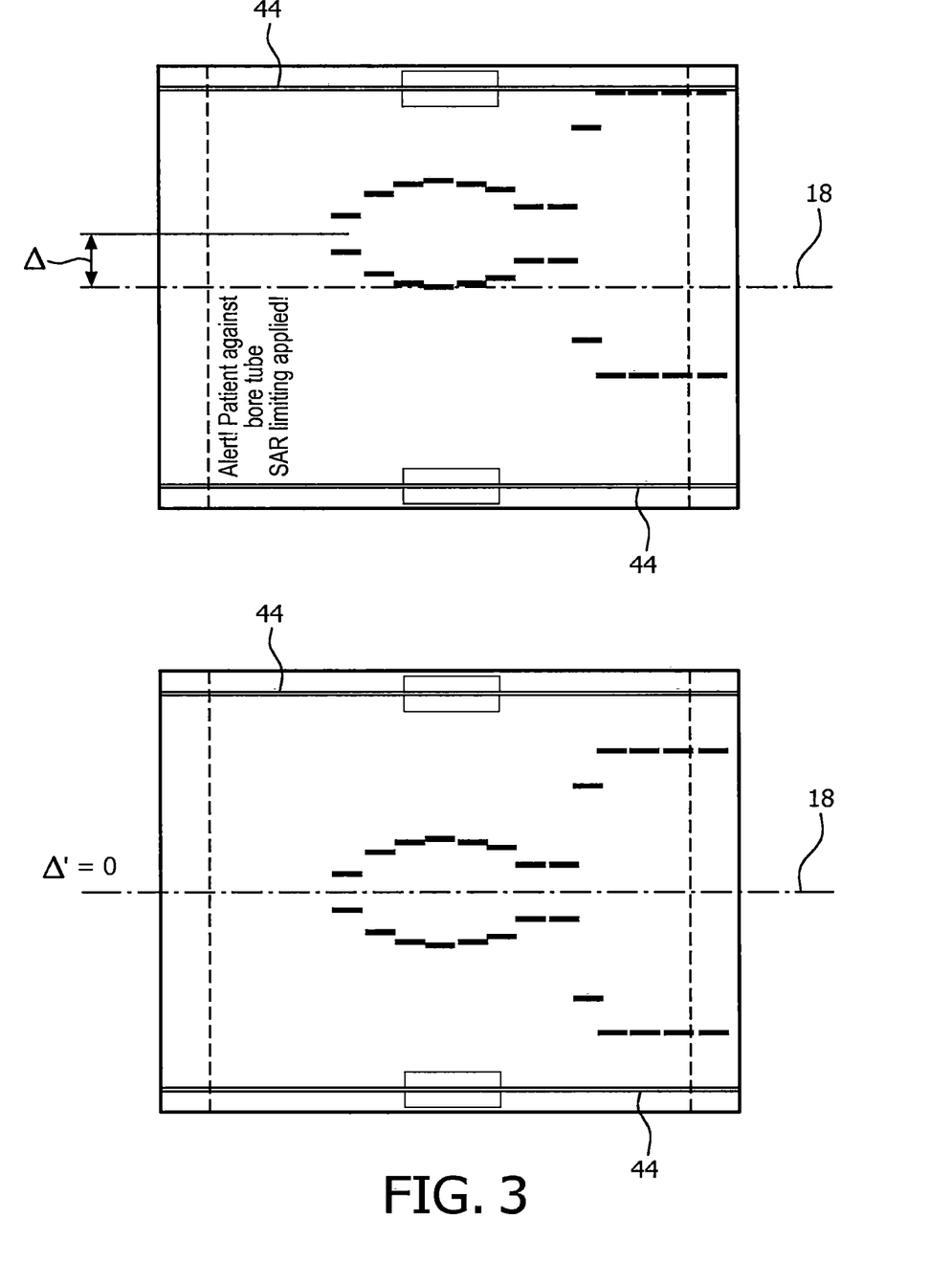
FIG. 3 illustrates geometric outlines of a subject of interest in two different positions relative to the radio frequency transmit antenna.

A lateral displacement Δ of the subject of interest 20 (FIG. 3) from the center axis 18 is given by $$\Delta = \underset{i}{\text{average}}(d_9(z_i) - d_1(z_i))$$

wherein the average is taken over a plurality of locations $z_i$ at which position parameters $d_1$, $d_9$ have been determined.

As the relative position of the proximity detectors $D_1$, $D_9$ with regard to the radio frequency transmit antenna 36 is exactly known, the determined position parameters $d_1$, $d_9$ are indicative of the position of at least the portion of the subject of interest 20 relative to the radio frequency transmit antenna 36.

While the subject of interest 20, being supported by the patient table 48, is crossing the entrance region 32 in the z-direction for being positioned within the examination space 16 for instance by assistance of an orderly, the two proximity detectors $D_1$, $D_9$ provide output signals to the control unit 26, which is configured to record the output signals at a specified sample rate and to determine position parameters $d_1$, $d_9$ from the recorded output signals.

In order to be able to carry out the method as a specific operation of the magnetic resonance imaging system 10, the control unit 26 comprises a software module 50 (FIG. 1). The method steps to be conducted are converted into a program code of the software module 50, wherein the program code is implementable in the memory unit 28 of the control unit 26 and is executable by a processor unit 30 of the control unit 26.

The determined position parameters $d_1$, $d_9$ and the lateral dimensions $w_i$ determined at the plurality of i locations $z_i$ are used by the control unit 26 to obtain data for generating a geometric outline of the subject of interest 20 relative to the radio frequency transmit antenna 36 of the magnetic resonance imaging system 10. This geometric outline is then displayed on the monitor unit for being checked by an operator (FIG. 3).

In a less complex embodiment of the method, the distances $d_{right}$ of the subject of interest 20 to the main magnet center bore wall 44 calculated from the determined position parameters $d_1$, $d_9$ are compared to a pre-determined value for a minimum distance to the main magnet center bore wall 44, for instance 5 mm, which is stored in the memory unit 28 of the control unit 26. The pre-determined value for the minimum distance to the main magnet center bore wall 44 is selected such that the specific absorption rate for the subject of interest 20 is kept well below the maximum tolerable value. The pre-determined value for the minimum distance can be visualized with a geometric outline of the subject of interest 20 on the monitor unit as information to the operator. The magnetic resonance imaging system 10 is equipped with an absolute position determination system (not shown) for the patient table 48, so that the geometric outline is not distorted by variations of the speed of positioning the subject of interest 20 within the examination space 16 by the orderly. FIG. 3 illustrates the geometric outline for the subject of interest 20 in a nominal position (left) with zero lateral displacement $\Delta'$ and in a position with a non-zero lateral displacement $\Delta$ (right).

If a calculated distance of the subject of interest 20 to the main magnet center bore wall 44 falls below the pre-determined value for a minimum distance, the control unit 26 is configured to adjust at least one radio frequency power-related parameter of radio frequency power to be fed to the radio frequency transmit antenna 36. The step of adjusting comprises adjusting at least one out of the duty cycle of the radio frequency pulse sequence and the radio frequency power amplitude. In this embodiment, the radio frequency power amplitude is adjusted by the control unit 26 by reducing to a pre-determined percentage of the planned radio frequency power amplitude, for example to 5%. By this approach it becomes possible to eliminate any need to place padding between the subject of interest 20 and the main magnet center bore wall 44 of the scanning unit 12.

Further, the control unit 26 is configured to invoke a warning signal, which is displayed on the monitor unit, to inform the operator about the need for repositioning the subject of interest 20 (FIG. 3).

In another embodiment of the method, the control unit 26 is provided with pre-determined relationships for a specific absorption rate being absorbed by a subject of interest 20 having specified lateral dimensions $w_i$ while being exposed to the transmitted radio frequency power at specified relative position parameters $d_i$. The pre-determined relationships have been obtained from simulations using the transmission characteristic of the radio frequency transmit antenna 36, known from either measurement or theoretical considerations.

The pre-determined relationships for the specific absorption rate could for instance be represented by two-dimensional lookup tables, wherein the two dimensions are given by the lateral dimension w and the lateral displacement $\Delta$ of the subject of interest 20, and wherein a relative scalar value is assigned to each possible combination of the two variables. With the simulation model assuming a reference lateral dimension, weight and lateral positioning of the subject of interest 20, an expected specific absorption rate for a subject of interest 20 having an individual lateral dimension w and being positioned with a specified lateral displacement $\Delta$ can readily be obtained by multiplying the value of the reference specific absorption rate with the assigned relative scalar value.

While lookup tables are described in this embodiment, alternatively, the pre-determined relationships for the specific absorption rate could be represented by a formula approximating the empirical relationships.

Then, by making use of determined position parameters $d_i$ and lateral dimensions $w_i$ of the subject of interest 20 and based on the pre-determined relationships, the control unit 26 is configured to determine an expected specific absorption rate of radio frequency power to be transmitted by the at least one radio frequency transmit antenna 36.

In the following, the determined expected specific absorption rate is then compared with a maximum tolerable specific absorption rate, given e.g. by IEC limits. The control unit 26 is configured to adjust at least one radio frequency power-related parameter of radio frequency power to be fed to the radio frequency transmit antenna 36 in dependence of the determined expected specific absorption rate. If the determined expected specific absorption rate falls below the maximum tolerable specific absorption rate, the control unit 26 is configured to allow the planned scan to proceed. If the determined expected specific absorption rate is equal to or exceeds the maximum tolerable specific absorption rate, the control unit 26 is configured to reduce the radio frequency power amplitude to comply with the safety regulations.

Figure 4:
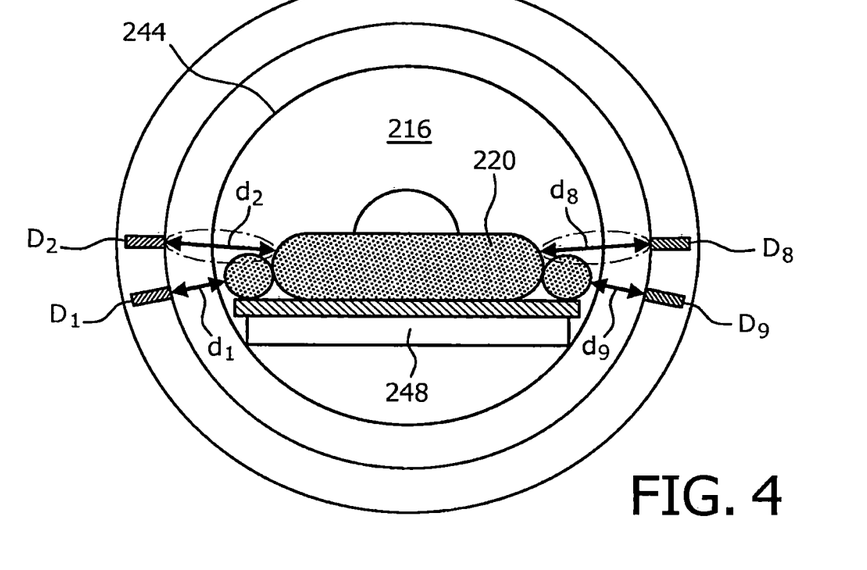
FIG. 4 depicts an alternative embodiment of a proximity detection unit including a plurality of four proximity detectors.
Figure 5:
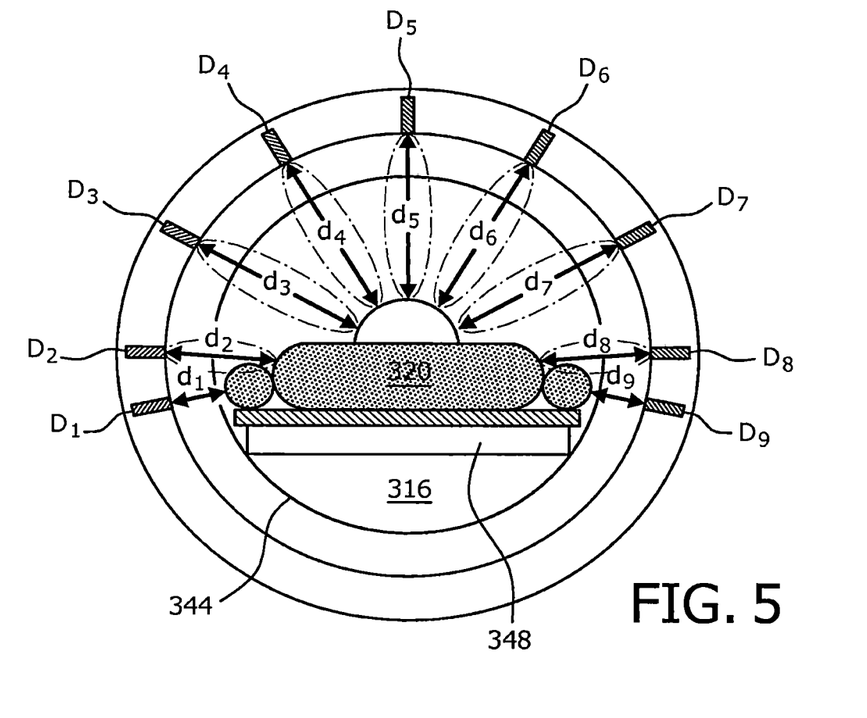
FIG. 5 shows another alternative embodiment of a proximity detection unit including a plurality of nine radially arranged proximity detectors.

The determining of the expected specific absorption rate can be refined by employing embodiments of a proximity detection unit pursuant to FIGS. 4 and 5. In the following, embodiments of a proximity detection unit in accordance with the invention are disclosed. The individual embodiments are described with reference to a particular figure and are identified by a prefix number of the particular embodiment. Features whose function is the same or basically the same in all embodiments are identified by reference numbers made up of the prefix number of the embodiment to which it relates, followed by the number of the feature. If a feature of an embodiment is not described in the corresponding figure depiction, or a reference number mentioned in a figure depiction is not shown in the figure itself, reference should be made to the description of a preceding embodiment.

FIG. 4 shows a partial frontal view of the scanning unit 212 of the magnetic resonance imaging system 210 pursuant to FIG. 1. In contrast to the embodiment illustrated by FIG. 2, the proximity detection unit 246 comprises a plurality of four proximity detectors $D_1$, $D_2$, $D_8$, $D_9$ designed as ultrasonic proximity sensors. Again, the proximity detectors $D_1$, $D_2$, $D_8$, $D_9$ are arranged in the entrance region 232 of the scanning unit 212. Each one of the four proximity detectors $D_1$, $D_2$, $D_8$, $D_9$ is aiming in a radial direction, i.e. perpendicular to and towards the center axis 218. Similar to the embodiment pursuant to FIG. 2, the four proximity detectors $D_1$, $D_2$, $D_8$, $D_9$ will determine the proximity of the subject of interest 220 during the crossing of the entrance region 232 by the subject of interest 220 for positioning within the examination space 216, but due to the larger number of proximity detectors $D_1$, $D_2$, $D_8$, $D_9$, the statistical error for determining position parameters $d_i$ and lateral dimensions $w_i$ of the subject of interest 220 is reduced.

FIG. 5 shows a partial frontal view of the scanning unit 312 of the magnetic resonance imaging system 310 pursuant to FIG. 1. In contrast to the embodiment illustrated by FIG. 2, the proximity detection unit 346 comprises a plurality of nine proximity detectors $D_1, \ldots, D_9$ designed as ultrasonic proximity sensors. Again, the proximity detectors $D_1, \ldots, D_9$ are arranged in the entrance region 332 of the scanning unit 312. Each one of the nine proximity detectors $D_1, \ldots, D_9$ is aiming in a radial direction, i.e. perpendicular to and towards the center axis 318. Similar to the embodiment pursuant to FIG. 2, the nine proximity detectors $D_1, \ldots, D_9$ will determine the proximity of the subject of interest 320 during the crossing of the entrance region 332 by the subject of interest 320 for positioning within the examination space 316.

In this state of operation, a plurality of pairs of proximity detectors obviously is arranged to aim towards the subject of interest 320 from two intersecting directions that form angles of at least 45°, for instance proximity detectors $D_1$ and $D_4$, and $D_6$ and $D_9$.

Besides the reduced statistical error for determining position parameters $d_i$ and lateral dimensions $w_i$ of the subject of interest 320, the radial arrangement of the plurality of nine proximity detectors $D_1, \ldots, D_9$ enables to determine a lateral dimension w' in a second direction that is independent of the direction of the earlier described lateral dimension w, and, by that, to provide an estimate of a cross-section of the subject of interest 320, which, in turn, allows for an improved determination of an expected specific absorption rate of radio frequency power by the subject of interest 320.

In yet another embodiment, which is not illustrated, a proximity detection unit comprises at least one proximity detector that is designed as a camera, either for single images or for series of images. The at least one camera is positioned and configured to determine a top view of the subject of interest when crossing the entrance region of the examination space, and/or to determine a frontal view of the subject of interest being positioned within the examination space.

The top view and/or frontal view of the subject of interest is then compared with a top view of the patient table without the subject of interest and/or a frontal view of the main magnet bore without the subject of interest being positioned within the examination space, respectively. Position parameters and lateral dimensions of the subject of interest can be determined by employing an image recognition software that resides within the control unit and is executable by the processor unit of the control unit.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST

| | |
|---|---|
| 10 | magnetic resonance imaging system |
| 12 | scanning unit |
| 14 | main magnet |
| 16 | examination space |
| 18 | center axis |
| 20 | subject of interest |
| 22 | magnetic gradient coil system |
| 24 | human interface device |
| 26 | control unit |
| 28 | memory unit |
| 30 | processor unit |
| 32 | entrance region |
| 34 | radio frequency shield |
| 36 | radio frequency transmit antenna |
| 38 | radio frequency switching unit |
| 40 | radio frequency transmitter |
| 42 | signal processing unit |
| 44 | center bore wall |
| 46 | proximity detection unit |
| 48 | patient table |
| 50 | software module |
| $B_0$ | static magnetic field |
| $B_1$ | radio frequency excitation field |
| $D_i$ | i-th proximity detector |
| $d_i$ | i-th position parameter |
| $w_i$ | i-th lateral dimension (width) |
| $d_b$ | bore diameter |
| $d_s$ | detector distance |
| $d_{left}$ | left distance |
| $d_{right}$ | right distance |
| $\Delta$ | lateral displacement |
| $z_i$ | locations |

The invention claimed is:

1. A magnetic resonance imaging system configured for acquiring magnetic resonance image data of at least a portion of a subject of interest, comprising:
   a bore defining a tubular examination space configured to receive at least the portion of the subject of interest within, the examination space having an entrance region for the subject of interest to enter the examination space;
   a main magnet configured for generating a static magnetic field B0 in the examination space;
   a magnetic gradient coil system configured for generating gradient magnetic fields superimposed on the static magnetic field B0 in the examination space;
   at least one radio frequency antenna configured for applying a radio frequency excitation field B1 to nuclei of or within the portion of the subject of interest for magnetic resonance excitation and for receiving magnetic resonance signals from the nuclei of or within the portion of the subject of interest that have been excited by applying the radio frequency excitation field B1;
   a patient table configured to move the subject through the entrance region and the examination space;
   at least one proximity detector disposed adjacent the entrance region and configured for determining a geometric parameter as the patient table moves the subject through the entrance region, the geometric parameter being indicative of a lateral width and a position parameter which is indicative of a position of at least the portion of the subject of interest relative to the at least one radio frequency antenna configured for applying the radio frequency excitation field B1; and
   a control processor configured to:
      adjust the radio frequency excitation field B1 to be applied to the subject of interest who moved through the entrance region to be imaged based on a lateral offset of at least the portion of the subject of interest relative to the at least one radio frequency antenna of the magnetic resonance imaging system that transmits the radio frequency excitation field B1 as measured by the at least one proximity detector disposed adjacent the entrance region, and adjust at least one radio frequency power-related parameter of radio frequency power to be fed to the at least one radio frequency antenna that transmits the radio frequency excitation field B1 solely in dependence on the position parameter and the determined geometric parameter of the subject of interest.

2. The magnetic resonance imaging system of claim 1, wherein the at least one proximity detector comprises a pair of proximity detectors arranged to aim towards the subject of interest from two intersecting directions that form angles of at least 45° to measure the lateral width of the subject.

3. The magnetic resonance imaging system of claim 1, wherein the at least one proximity detector is a camera.

4. The magnetic resonance imaging system of claim 1, wherein the at least one proximity sensor works on an optical or acoustic principle and not on a magnetic resonance principle.

5. The magnetic resonance imaging system of claim 1, wherein the control processor is further configured to determine a local specific absorption rate based on a lateral width of at least the portion of the subject.

6. The magnetic resonance imaging system of claim 5, wherein the processor is further configured to determine the local specific absorption rate based on the lateral offset of the subject.

7. The magnetic resonance imaging system of claim 5, wherein the control processor is further configured to adjust RF transmit power to maintain the local specific absorption rate below a preselected limit.

8. The magnetic resonance imaging system of claim 1, wherein the control processor is configured to determine the local specific absorption rate based on the lateral width of at least the portion of the subject and the lateral offset.

9. The magnetic resonance imaging system of claim 1, wherein the control processor is configured to control power of the radio frequency excitation field B1 for the magnetic resonance excitation of the nuclei based on both the lateral width of the subject and the lateral offset.

10. A method of adjusting a radio frequency excitation field B1 to be applied to a subject of interest during magnetic resonance imaging, the method comprising:

moving a subject supported in a prone position on a patient table into a magnetic resonance examination space of a bore of a magnetic resonance imaging system in a radio frequency antenna configured to apply the radio frequency excitation field B1 to nuclei within a portion of the subject disposed in the magnetic resonance examination space;

as the subject is moved into the examination space, determining a lateral width w of the subject;

determining a lateral displacement Δ of the subject from a center axis of the bore; and adjusting radio frequency power applied to the radio frequency antenna based solely on both the lateral width w and the lateral displacement Δ.

* * * * *